(12) United States Patent
Street

(10) Patent No.: US 6,489,619 B2
(45) Date of Patent: Dec. 3, 2002

(54) PIXEL CIRCUIT WITH SELECTABLE CAPACITOR LOAD FOR MULTI-MODE X-RAY IMAGING

(75) Inventor: Robert A. Street, Palo Alto, CA (US)

(73) Assignee: Xerox Corporation, Stamford, CT (US)

(*) Notice: Subject to any disclaimer, the term of this patent is extended or adjusted under 35 U.S.C. 154(b) by 13 days.

(21) Appl. No.: 09/844,382

(22) Filed: Apr. 27, 2001

(65) Prior Publication Data
US 2002/0158206 A1 Oct. 31, 2002

(51) Int. Cl.[7] .................................................. G01T 1/24

(52) U.S. Cl. .......................... 250/370.09; 250/370.01; 250/370.08

(58) Field of Search ...................... 250/370.01, 370.08, 250/370.09, 370.14, 371; 257/443, 444, 448

(56) References Cited

U.S. PATENT DOCUMENTS

| 4,785,186 A | | 11/1988 | Street et al. | 250/370.14 |
| 5,869,837 A | * | 2/1999 | Huang | 250/370.09 |
| 5,936,230 A | | 8/1999 | Street | 250/214 VT |
| 5,962,856 A | | 10/1999 | Zhao et al. | 250/370.09 |

OTHER PUBLICATIONS

Article entitled "Image Sensors In TFA Technology—Status And Future Trends", pp. 327–338, taken from Materials Research Society, vol. 507.
Article entitled "Large Area Image Sensor Arrays", Technology and Applications of Amorphous Silicon, edited by R.A. Street, Springer Series in Materials Science 37, Chapter 4, p. 147.

* cited by examiner

Primary Examiner—Constantine Hannaher
Assistant Examiner—Timothy J. Moran
(74) Attorney, Agent, or Firm—Bever, Hoffman & Harms, LLP; Patrick T. Bever

(57) ABSTRACT

Each pixel of an image sensor array includes a capacitive load that is selectively coupled to or decoupled from the usual sensor capacitance to facilitate dual mode operation. During a first operating mode (e.g., a high-power operating mode such as radiography), a global enable signal is asserted to turn on a mode control transistor of each pixel that couples the selectable capacitive load to the sensor, thereby increasing the total capacitance of the pixels. During a second operating mode (e.g., a low-power operating mode such as fluoroscopy), the global enable signal is de-asserted, thereby decoupling the optional capacitive load from the sensor to minimize pixel capacitance. An amorphous silicon sensor includes an additional metal plate located below the lower sensor plate to provide the optional capacitive load. The additional metal plate is formed from the same metal layer that is used to fabricate the gate lines of the array.

20 Claims, 3 Drawing Sheets

PIXEL CIRCUIT WITH SELECTABLE CAPACITOR LOAD FOR MULTI-MODE X-RAY IMAGING

FIELD OF THE INVENTION

This invention relates to the field of imaging devices, and in particular to those devices containing a sensor array. The invention is most particularly applicable to an amorphous silicon X-ray image sensor array usable for both fluoroscopic and radiographic imaging operations.

BACKGROUND OF THE INVENTION

Two-dimensional sensor arrays are well-known devices for real time imaging of incident high energy radiation (see R. A. Street et al., "Large Area Image Sensor Arrays", in Technology and Applications of Amorphous Silicon, Editor R. A. Street, Springer Series in Materials Science 37, Springer-Verlag, Berlin, 2000, chapter 4, p. 147, for a general description of the structure of the arrays). Such sensor arrays are particularly advantageous for X-ray imaging because they present a relatively large size image sensor array. Each sensor operates on the principal of integrating a charge representative of the quantities of ionizing radiation incident on the sensor. In the direct detection approach, incident high-energy radiation (e.g., X-ray photons) is directly converted to a charge by the sensor. In the indirect detection approach, a phosphor converter absorbs high energy radiation (e.g., X-ray photons) and generates a proportional amount of visible light that is then converted to a charge by the sensor.

Despite the development of recent medical imaging modalities, such as computed tomography (CT), ultrasound, nuclear medicine and magnetic resonance imaging (MRI), all of which are digital, X-ray imaging systems remain an important tool for medical diagnosis. Although the majority of X-ray imaging systems in current use are of analog design, digital radiology is an area of considerable recent growth. Digital radiology provides significant advantages over its analog counterpart, such as easy comparison of radiological images with those obtained from other imaging modalities, the ability to provide image networking within a hospital for remote access and archiving, facilitating computer aided diagnosis by radiologists, and facilitating teleradiology (i.e., remote diagnostic service to poorly populated regions from a central facility).

Digital radiology provides two dominant modes of imaging that have different operational characteristics. In radiography, a single image frame is acquired under conditions of a large signal (e.g., using a relatively high X-ray dose). In fluoroscopy, frames are acquired at typically 30 or 60 frames per second and the signal (e.g., X-ray dose) is small, at least 10–100 times lower than that used in radiography.

It is highly desirable for an imaging device to perform both radiography and fluoroscopy functions. Apart from the cost benefits associated with a single imager that performs both radiography and fluoroscopy functions, such an imager is needed by the radiologist to rapidly switch between the low contrast, low dose fluoroscopic mode and a radiographic mode to obtain high contrast images. It is also highly desirable to perform various fluoroscopy operations using various intermediate intensities (i.e., between the conventional fluoroscopic and radiographic intensities).

While image sensors utilized to perform fluoroscopic and radiographic operations are generally reasonably compatible, there are some conflicts in the design approach, particularly concerning the pixel capacitance that stores the image charge and also generates electronic noise. The saturation signal for an image sensor pixel is given by $C_S V_{MAX}$, where $C_S$ is the capacitance of the pixel and $V_{MAX}$ is the maximum voltage to which the capacitance can be charged. For a typical sensor array that uses an amorphous silicon (a-Si:H) photodiode as the pixel sensor, the capacitance is 1–2 pF for a pixel size in the 100–200 micron range using a 5 V bias voltage. The maximum pixel charge of 5–10 pC is comfortably enough for radiography but greatly exceeds the requirements for fluoroscopy.

Large pixel capacitance would not be a problem for fluoroscopy except that it contributes to electronic noise. There are many contributions to the noise of an imager, but the one that is ultimately impossible to overcome with present array designs is the kTC noise of the pixel, which arises from the thermal noise of the resistance of the switching transistor, and whose magnitude is entirely determined by the pixel capacitance. Therefore, it is not possible to efficiently utilize a conventional pixel for both fluoroscopic and radiographic imaging because the large capacitance needed to perform radiography produces too much noise when the same pixel is utilized for fluoroscopy.

What is needed is a single image sensor that can be optimized for both fluoroscopic and radiographic operating modes.

SUMMARY OF THE INVENTION

The present invention is directed to an imaging apparatus in which each pixel of a sensor array includes one or more capacitor loads that are selectively coupled to or decoupled from the usual sensor capacitance to facilitate multi-mode operation. This selectable capacitor load arrangement provides a method for reducing the electronic noise in, for example, a-Si:H medical imagers during fluoroscopy operation, while maintaining the high dynamic range required for radiography.

Each pixel circuit of the imaging apparatus includes a sensor connected between a bias voltage and a first transistor, which is controlled by a gate line to pass collected image data to a data line, and one or more capacitor circuits that include the selectable capacitor load and mode control transistor connected in series between the sensor and ground. The mode control transistors are controlled by a global enable signal that determines the operating mode of image sensor array. When a global enable signal is asserted (e.g., during a radiographic operating mode), a selected mode control transistor of each pixel is turned on, thereby coupling the associated additional capacitor load to the sensor (i.e., effectively increasing the total capacitance) of each pixel. When the selected global enable signal is subsequently de-asserted (e.g., during a fluoroscopic operating mode), the associated mode control transistor of each pixel is turned off, thereby isolating the additional capacitor load from the sensor (i.e., effectively decreasing electronic noise). Accordingly, a single sensor array is provided that is selectively optimized for multi-mode operations.

In accordance with an embodiment of the present invention, an a-Si:H sensor is modified to include the selectable capacitor load by providing a third plate below the lower (second) plate of the sensor. The third plate is etched from the same metal layer used to form the gate line for accessing the select transistor of the pixel, thereby minimizing the number of additional process steps required to provide the selectable capacitor load. The third plate is selectively coupled to a ground line during high-capacitance operations (e.g., radiography) by a thin film transistor (TFT).

BRIEF DESCRIPTION OF THE DRAWINGS

These and other features, aspects and advantages of the present invention will become better understood with regard to the following description, appended claims, and accompanying drawings, where:

DETAILED DESCRIPTION OF THE DRAWINGS

Figure 1A:
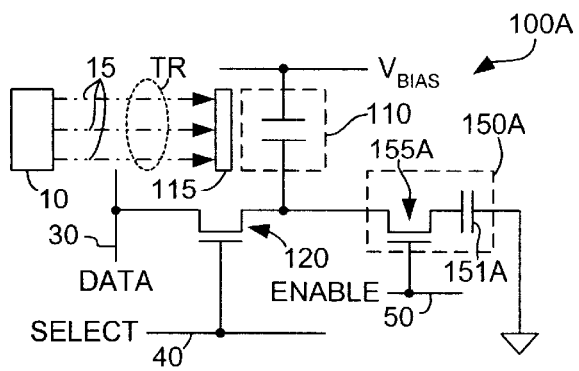
FIGS. 1A and 1B are simplified diagrams showing respective variations of a pixel circuit according to a first embodiment of the present invention.

FIG. 1A shows a portion of an imaging apparatus that includes a source 10 of high-energy radiation beams 15, and an array of several thousand pixel circuits 100A (one shown) that are arranged in rows and columns and accessed using known techniques. In general, the array of pixels 100A generates a "negative" image of an object (not shown) placed in a target region TR by detecting radiation beams 15 that are not blocked by the object.

Each pixel circuit 100A includes a sensor 110, a phosphor converter 115 located between sensor 110 and source 10, a select (first) transistor 120, and a capacitor circuit 150A. Phosphor converter 115 operates as described above to facilitate indirect imaging of an object (not shown) located in target region TR. Sensor 110 has a first terminal connected to a bias voltage line (first voltage source) $V_{BIAS}$, and a second terminal connected to a first terminal 121 of select transistor 120. The second terminal of select transistor 120 is connected to a data line 30 that transmits a DATA signal from sensor 110, and a gate terminal of select transistor 120 is connected to a gate line 40 that receives a control (SELECT) signal. Capacitor circuit 150A is connected between terminal 121 of select transistor 120 and ground (or other voltage source), and includes a capacitor 151A connected in series with an enable (second) transistor 155A. Enable transistor 155A is controlled by a global ENABLE signal that is simultaneously transmitted on a global enable line 50 to all pixel circuits 100A of the array. Accordingly, global ENABLE signal is utilized to switch capacitor circuit 150A between an enabled (high capacitance) mode, in which capacitor 151A is coupled to sensor 110, and a disabled mode, in which capacitor 151A is decoupled (isolated) from sensor 110.

Pixel circuit 100A generally operates as part of an active matrix X-ray imaging apparatus in the following manner. High-energy X-ray beams 15 are directed toward an object placed in target region TR. Those X-ray beams 15 that are not blocked or otherwise deflected by the object strike phosphor converter 115, which generates visible light that enters sensor 110, which acts as a charge integrator. As light enters from phosphor converter 115, sensor 110 stores the corresponding charge until select transistor 120 is switched on. In other words, sensor 120 operates in a first phase where it merely accumulates a charge representative of the amount of visible light received from phosphor converter 115, and then operates in a second "readout" phase when the SELECT signal is pulsed high on gate line 40, which turns on all the gates of those select transistor 120 in a column of the array to which the particular pulsed gate line 40 is attached. The SELECT pulse causes the charges on each sensor 110 to be transferred to an associated data line 30 for that column of sensors 110, which is connected to external circuitry (not shown) that determines the amount of charge collected by sensor 110 in accordance with known techniques. Such an output essentially resets sensor 110 back to its full bias and the charge collection process is restarted. Typically, once one column has been read out, the next column is immediately pulsed so that the entire array is sequentially read out from one side to the other.

In addition to the basic operation of sensor 110 and select transistor 120, described above, capacitor circuit 150A allows pixel 100A to selectively operate in either a high-capacitance mode or a low-capacitance mode. Specifically, when the global ENABLE signal is asserted, mode control transistor 155A of each pixel circuit 150A is turned on, thereby coupling capacitor 151A to sensor 110 (i.e., effectively increasing the total capacitance of pixel circuit 100A). With capacitor 151A coupled to sensor 110, the charge collected by sensor 110 is relatively large, thereby optimizing pixel circuit 100A for high-capacitance operation such as, for example, radiographic imaging operations. When the global ENABLE signal is subsequently de-asserted, mode control transistor 155A is turned off, thereby isolating capacitor 151A from sensor 110, thereby effectively minimizing the total capacitance of pixel circuit 100A for low-noise operation (e.g., for fluoroscopic imaging operations). Accordingly, by providing capacitor circuit 150A that selectively couples capacitor 151A to or decouples capacitor 151A from sensor 110, pixel circuit 100A is able to perform both radiographic and fluoroscopic operations using a single sensor array.

Figure 1B:
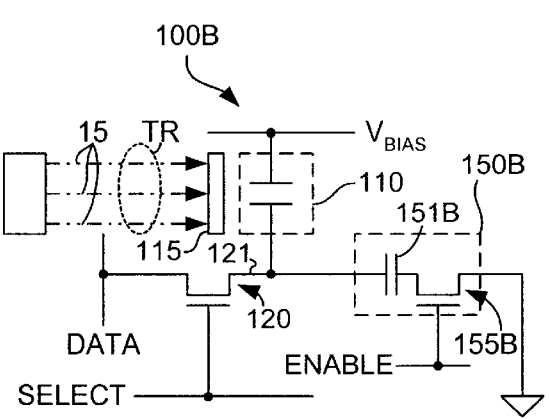

FIG. 1B shows a pixel circuit 100B according to a practical variation of the first embodiment. Pixel circuit 100B differs from pixel circuit 100A (FIG. 1A) in that mode control transistor 155B is connected between capacitor 151B and ground (i.e., one plate of capacitor 151B is directly coupled to one plate of sensor 110). As described below with reference to FIG. 4, the arrangement shown in FIG. 1B is more practical in a-Si:H sensor applications because this allows capacitor 151B to share one plate with sensor 110. The operation of pixel circuit 100B is essentially identical to that described above with reference to pixel circuit 100A.

Figure 2:
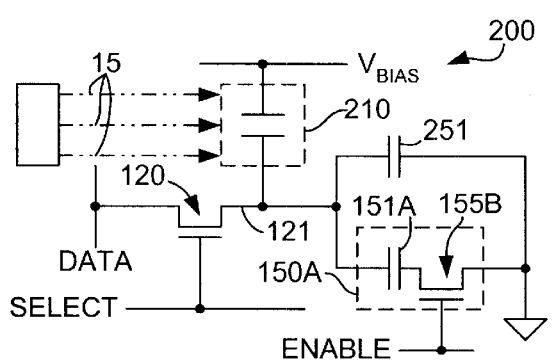
FIG. 2 is a simplified diagram showing a pixel circuit according to a second embodiment of the present invention.

FIG. 2 shows a pixel circuit 200 according to a second embodiment of the present invention. Pixel circuit 200 is utilized in a direct detection imaging apparatus in which high-energy radiation beams 15 are directly transmitted to sensors 210 of pixels 200 (one shown). That is, unlike the indirect imaging approach shown in FIGS. 1A and 1B, direct imaging apparatus do not utilize a phosphor converter. This direct approach typically requires that sensor 210 be formed using a selenium, mercury iodide or lead iodide layer, or a relatively thick a-Si:H layer (i.e., compared to that needed in the indirect approach, described above), and therefore has a relatively small capacitance. To increase the capacitance of pixel circuit 200, an additional capacitor 251 is added between first terminal 121 of select transistor 120 and ground. Capacitor circuit 150B (or, in another embodiment not shown, capacitor circuit 150A) is connected in parallel with fixed capacitor 251, and facilitates dual mode operation in the manner described above. As described below with reference to FIG. 5, fixed capacitor 251 and additional capacitor 151B can be readily implemented by a split metal layer formed under sensor 210 such that the fluoroscopy mode capacitance and the radiography mode capacitance have suitably chosen values, perhaps differing by a factor 5 or more.

Figure 3:
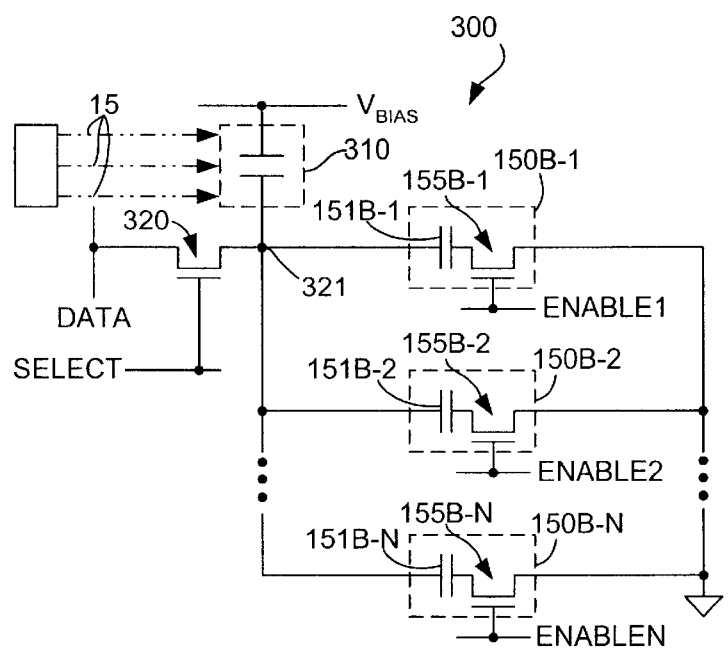
FIG. 3 is a simplified diagram showing a pixel circuit according to a third embodiment of the present invention.

FIG. 3 shows a pixel circuit 300 according to a third embodiment of the present invention. Pixel circuit 300 includes a sensor 310 connected to a first terminal 321 of a select transistor 320, and multiple capacitor circuits 150B-1 through 150B-N that are connected in parallel between terminal 321 and ground. Each capacitor circuit 150B-1 through 150B-N includes a capacitor and a mode control transistor that is controlled by a separate control signal, thereby facilitating multiple operating modes and/or the ability to adjust pixel capacitance to optimize a selected operating mode. For example, capacitor circuit 150B-1 includes a mode control transistor 155B-1 that is controlled by a first control signal ENABLE1 to selectively couple capacitor 151B-1 to and decouple capacitor 151B-1 from sensor 310. Similarly, mode control transistor 155B-2 of capacitor circuit 150B-2 is controlled by a second control signal ENABLE2, and mode control transistor 155B-N of capacitor circuit 150B-N is controlled by an nth control signal ENABLEN. In operation, the total capacitance of sensor 310 is adjusted to a desired level by asserting one or more selected control signals. In one possible embodiment, each capacitor 151B-1 through 151B-N provides a different capacitive load (e.g., capacitor 151B-1 is smaller than capacitor 151B-2, etc.), thereby facilitating fine adjustment of the total pixel capacitance by selecting a corresponding combination of capacitive loads.

Figure 4:
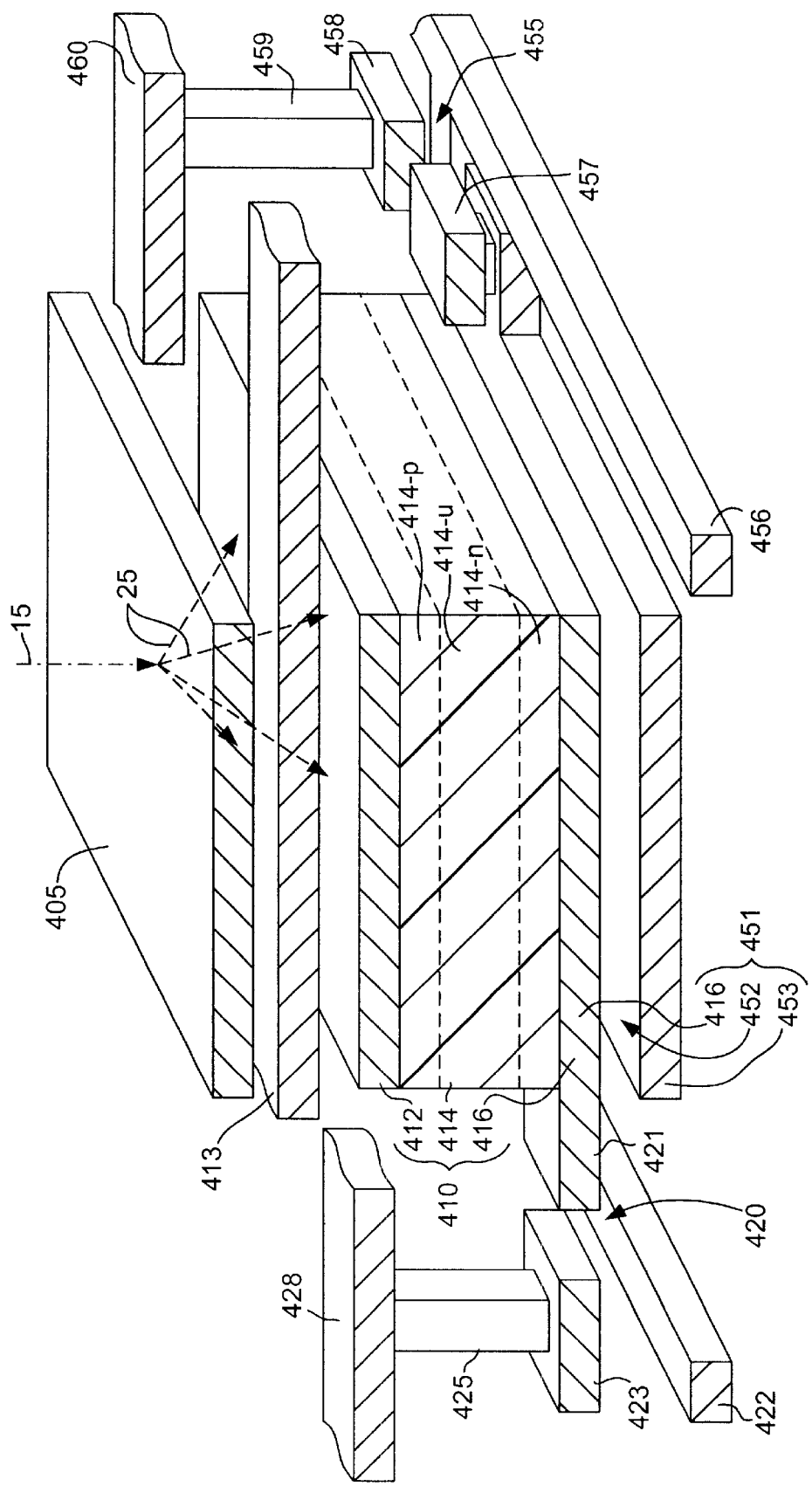
FIG. 4 is a front perspective view showing a simplified pixel structure according to a fourth embodiment of the present invention.

FIG. 4 is a simplified perspective view showing a pixel structure 400 according to a fourth embodiment of the present invention. Pixel structure 400 includes a phosphor converter 405 positioned over an a-Si:H sensor 410, which in turn is located over an additional, selectable capacitor 451. Note that passivation (insulation) layers are omitted from FIG. 4 to facilitate the following description.

Referring to the upper portion of FIG. 4, pixel structure 400 facilitates indirect detection in that phosphor converter 405 converts incident high-energy beams 15 into light beams 25 that are passed into sensor 410.

Sensor 410 includes an a-Si:H (charge sensing) layer 414 sandwiched between an upper metal plate (conductive layer) 412 and a lower metal plate (conductive layer) 416. A-Si:H layer 414 includes a thin p-type doped upper layer 414-p located next to upper plate 412, a thicker undoped middle layer 414-u, and a thin n-type doped lower layer 414-n located next to lower plate 416. Upper layer 414-p, middle layer 414-u, and lower layer 414-n are formed according to known practices, and the order of upper layer 414-p and lower layer 414-n can be reversed (i.e., with n-type doping in the upper layer and p-type doping in the lower layer). Upper plate 412 contacts a bias (metal) line 413, and is formed from a conductive transparent material (e.g., Indium-Tin Oxide (ITO)) to facilitate transmission of light beams 25 into doped a-Si:H layer 414. Lower plate 416 (e.g., metal) includes a portion 421 that forms a first terminal of a thin film transistor (TFT) (select transistor) 420. A gate line (electrode) 422 extends under first terminal 421 and a second terminal 423, which is connected by a metal via 425 to a data line 428. In an alternative embodiment to that shown in FIG. 4, data line 428 and ground line 460 are formed using the same metal layer used to form terminals 423 and 458, instead of the metal layer used to form bias line 413, thereby eliminating metal vias 425 and 459. During operation, charge stored in a-Si:H layer 414 is passed to data line 428 by transmitting an appropriate select signal on gate line 422.

Sensor 410 also includes a capacitor circuit formed by a capacitor 451 and a TFT (mode control transistor) 455. Capacitor 451 is formed by lower plate 416 of sensor 410 and a third plate 453 that is separated from lower plate 416 by a passivation (insulation) layer 452. Mode control transistor 455 is located at the right-most portion of FIG. 4, and controlled by mode control line 456. A first terminal 457 of mode control transistor 455 is connected to third plate 453, and a second terminal 458 of mode control transistor 455 is connected by a metal via 459 to a ground line 460.

As discussed above, the capacitance of conventional a-Si:H sensors is selected to facilitate either radiographic or fluoroscopic imaging operations. When imaging is performed using the indirect detection approach (i.e., using a phosphor converter), an a-Si:H layer having a thickness of approximately 1 micron typically provides sufficient capacitance to store enough charge for radiographic imaging operations, and an a-Si:H layer having a thickness of approximately 5 microns facilitates fluoroscopic imaging operations.

In accordance with an aspect of the present invention, pixel structure 400 facilitates both radiographic and fluoroscopic imaging by forming a relatively thick sensor 410 (e.g., using an a-Si:H layer 414 having a thickness of approximately 5 microns) that is optimized for fluoroscopic imaging, and selectively coupling capacitor 451 to increase total pixel capacitance to facilitate radiographic imaging. The thickness of a-Si:H layer 414 is determined, in part, by the difficulty of depositing and processing the a-Si:H. Increasing the thickness of a-Si:H layer 414 from 1 micron to approximately 5 microns produces a corresponding 5-fold reduction in the fluoroscopy kTC noise, thereby facilitating excellent fluoroscopic performance. The thicker a-Si:H layer 414 will result in some increase in image lag, and so the actual thickness used may be a compromise between the relative merits of reduced noise and reduced lag. The amount of lag will also depend on the applied bias voltage transmitted on bias line 413, which can also be optimized to a suitable value. The total sensor capacitance could be reduced by fabricating a smaller area sensor (i.e., reducing the size of the window defined in a passivation layer (not shown) located between lower layer 416 and a-Si:H layer 414, thereby reducing the contact area between lower plate 416 and a-Si:H layer 414), but this will reduce the overall array sensitivity, and may reduce the imager performance. Techniques to evaluate the actual imager performance are well established, so that it is possible to calculate an optimum thickness and sensor area for a particular pixel size and application.

In another embodiment (not shown), an organic sensor formed by a tetraphenyldiamine (TPD) hole transport layer on top of a benzimidazole perylene (BZP) generator layer is used in place of a-Si:H layer 414. First, the BZP charge generation layer is deposited by vacuum evaporation to a thickness of, e.g., 300 nm. The TPD hole transport layer, formed in a polycarbonate binder, is spin-coated to a thickness of, e.g., 10 micrometer. The TPD loading gives a hole mobility of about $10^{-5}$ cm$^2$/Vsec, without causing significant light scattering. The two-layer structure is advantageous as the independent control over the generation and transport layers allows flexibility in the choice of thickness (and hence, pixel capacitance), single carrier charge collection and low dark current. Other organic sensor materials may also be utilized.

In accordance with another aspect of the present invention, third plate 453, which forms the lower plate of capacitor 451, is formed using the same metal layer used to form gate line 422 and enable line 456, thereby facilitating the fabrication of pixel structure 400 without introducing additional processing steps. The contacts of transistor 455 (i.e., terminals 456 and 458) are likewise formed using the same source/drain metal layer used to form lower plate 416 and terminals 421 and 423 of transistor 420. Note that the space needed for enable line 456 is relatively small in comparison to the large pixel size (e.g., 100 to 200 microns per side) needed to facilitate fluoroscopic imaging. Further, because direct detection arrays and the recently developed high fill factor arrays have essentially 100% fill factor, the addition of enable line 456 will not reduce the sensitivity of these type of arrays.

Figure 5:
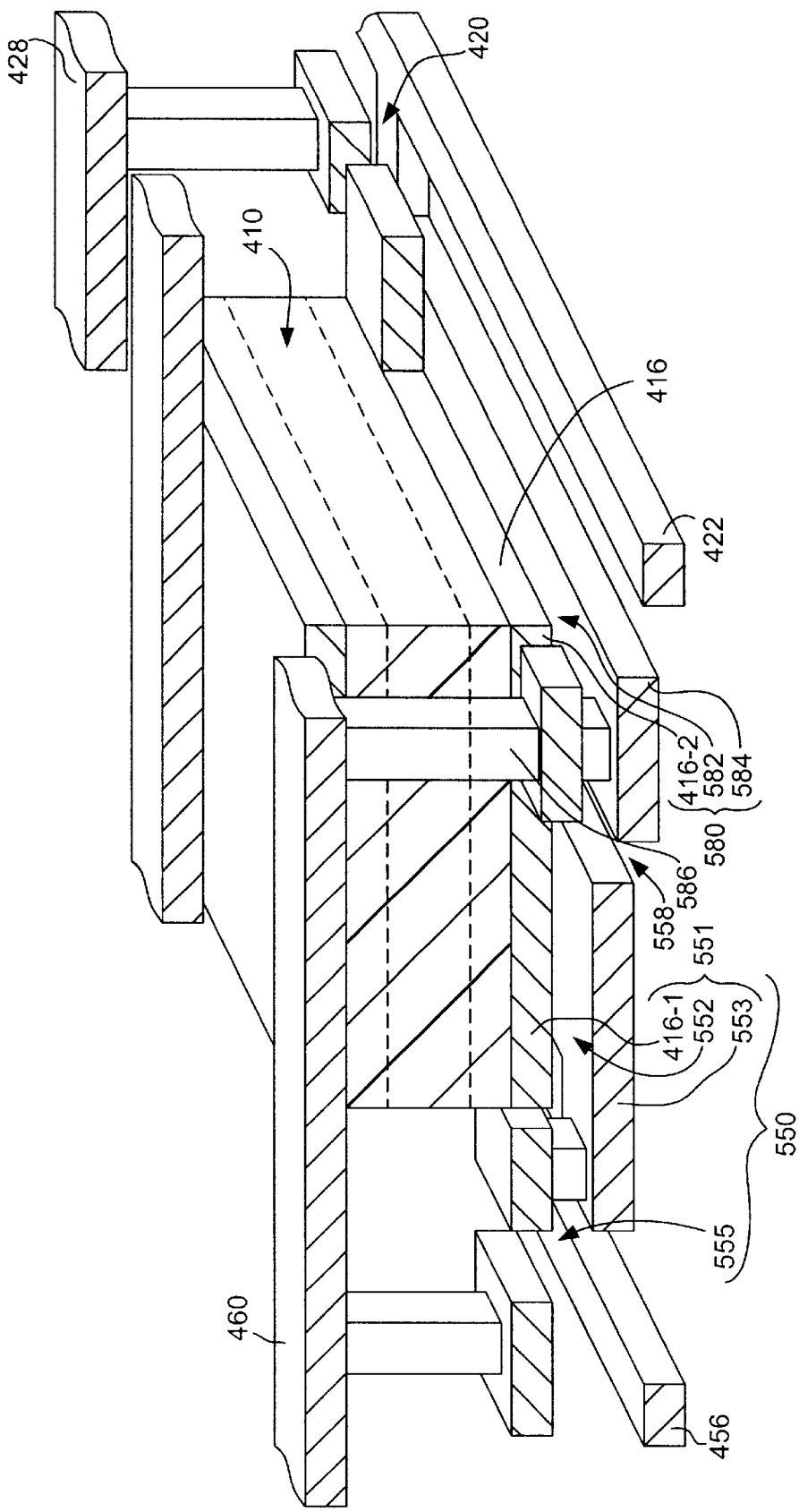
FIG. 5 is a rear perspective view showing a pixel structure according to a fifth embodiment of the present invention.

FIG. 5 is a rear perspective view showing a pixel structure 500 according to a fifth embodiment of the present invention. Pixel structure 500 includes sensor 410 and select transistor 420, which are essentially identical to those described above with reference to pixel structure 400 (see FIG. 4). However, unlike pixel structure 400, pixel structure 500 includes both a capacitor circuit 550 and a fixed capacitor 580 that are connected in parallel in the manner indicated above with reference to pixel circuit 200 (see FIG. 2). Capacitor 551 is similar to capacitor 451, described above, in that it is formed by a first portion 416-1 of lower layer 416, a passivation region 552, and a third (gate metal) plate 553. Capacitor circuit 550 also includes a mode control transistor 555 that is provided between third plate 553 and ground line 460, and is controlled by mode control line 456. Fixed capacitor 580 is formed by a second portion 416-2 of lower layer 416, a passivation region 582, and a fourth (gate metal) plate 584 that is separated from third plate 553 by a gap 558. Fourth plate 584 is connected to ground line 460 by a via structure 586. Accordingly, pixel structure 500 provides both fixed capacitor 580 and selectable capacitor 551 without significant change to the fabrication process by providing split (separated) metal layer portions 416-1 and 416-2, both being formed from the same metal layer as that used to form gate line 422 and mode control line 456.

Although the present invention has been described with respect to certain specific embodiments, it will be clear to those skilled in the art that the inventive features of the present invention are applicable to other embodiments as well. For example, FIGS. 4 and 5 illustrate only two of many possible pixel layouts that produce the pixel circuits described herein, and also illustrates that the layout can be accomplished with minimal additional processing. It is readily appreciated that separation of metal layer 416 into further portions, combined with one or more additional mode control lines, would provide the multiple capacitor circuit structure shown in FIG. 3. Those familiar with semiconductor processing will recognize that additional layout designs can be utilized without departing from the spirit and scope of the invention described herein.

What is claimed is:

1. An imaging apparatus including a sensor array having a plurality of pixel circuits and control circuitry for detecting electrical signals from the pixel circuits representative of radiation incident on the pixel circuits, wherein each pixel circuit comprises:
   a sensor having a first terminal connected to a first voltage source;
   a first transistor connected between a second terminal of the sensor and a data line; and
   a capacitor circuit including a first capacitor connected in series with a second transistor between the second terminal of the sensor and a second voltage source.

2. The imaging apparatus according to claim 1, wherein the first capacitor is connected between the second transistor and the second voltage source.

3. The imaging apparatus according to claim 1, wherein the second transistor is connected between the first capacitor and the second voltage source.

4. The imaging apparatus according to claim 1, wherein the sensor comprises:
   a first conductive layer connected to a first terminal of the first transistor;
   a charge sensing layer formed on the first conductive layer; and
   a second conductive layer formed over the charge sensing layer.

5. The imaging apparatus according to claim 4, wherein the charge sensing layer comprises at least one of amorphous silicon, selenium, lead iodide, benzimidazole perylene, and tetraphenyldiamine.

6. The imaging apparatus according to claim 4, wherein the first capacitor comprises a third conductive layer formed below the first conductive layer and connected to a first terminal of the second transistor.

7. The imaging apparatus according to claim 6, wherein a gate of the first transistor is formed by a first metal line;
   wherein a gate of the second transistor is formed by a second metal line; and
   wherein the third conductive layer, the first metal line, and the second metal line are etched from a single metal layer.

8. The imaging apparatus according to claim 1, further comprising a second capacitor connected in parallel with the capacitor circuit between the second terminal of the sensor and the second voltage source.

9. The imaging apparatus according to claim 8, wherein the sensor comprises:
   a first conductive layer connected to a first terminal of the first transistor;
   a charge sensing layer formed on the first conductive layer; and
   a second conductive layer formed over the charge sensing layer,
   wherein the first capacitor comprises a third conductive layer formed below a first region of the first conductive layer and connected to a first terminal of the second transistor, and
   wherein the second capacitor comprises a fourth conductive layer formed below a second region of the first conductive layer and connected to the second voltage source.

10. The imaging apparatus according to claim 9,
    wherein a gate of the first transistor is formed by a first metal line,
    wherein a gate of the second transistor is formed by a second metal line, and
    wherein the third conductive layer, the fourth conductive layer, the first metal line, and the second metal line are etched from a single metal layer.

11. The imaging apparatus according to claim 1, further comprising a second capacitor circuit connected in parallel with the capacitor circuit between the second terminal of the sensor and the second voltage source, the second capacitor circuit including a second capacitor connected in series with a third transistor.

12. The imaging apparatus according to claim 1, further comprising a phosphor converter mounted between the sensor and a source of high-energy radiation beams.

13. The imaging apparatus according to claim 1, wherein the first and second transistors comprise thin-film transistors.

14. A pixel circuit comprising:

a sensor;

a first transistor having a first terminal connected to the sensor and a second terminal connected to a data line; and a capacitor circuit connected between the first terminal of the first transistor and a voltage source, the capacitor circuit including a capacitor connected in series with a second transistor.

15. The pixel circuit according to claim 14, wherein the second transistor is connected between the capacitor and the first terminal of the first transistor.

16. The pixel circuit according to claim 14, wherein the capacitor is connected between the second transistor and the first terminal of the first transistor.

17. The pixel circuit according to claim 14, further comprising a second capacitor connected in parallel with the capacitor circuit between the first terminal of the first transistor and the voltage source.

18. The pixel circuit according to claim 14, further comprising a second capacitor circuit connected in parallel with the capacitor circuit between the first terminal of the first transistor and the voltage source, the second capacitor circuit including a second capacitor connected in series with a third transistor.

19. The pixel circuit according to claim 14, wherein the sensor comprises:

a first conductive layer connected to the first terminal of the first transistor;

a charge sensing layer formed on the first conductive layer; and a second conductive layer formed over the charge sensing layer.

20. A method for selectively operating a sensor array in one of a radiographic mode or and fluoroscopic mode, the sensor array having a plurality of pixel circuits, each pixel circuit including a sensor and a capacitor circuit including a capacitor connected in series with a mode control transistor between the sensor and ground, the method comprises:

during the radiographic mode, setting a total capacitance of each pixel circuit to a relatively high capacitance level by turning on the mode control transistor to couple the sensor of each pixel circuit to the capacitor of said each pixel circuit; and during the fluoroscopic mode, setting the total capacitance of each pixel circuit to a relatively low capacitance level by turning off the mode control transistor, thereby decoupling the capacitor from the sensor of each pixel circuit.

* * * * *

UNITED STATES PATENT AND TRADEMARK OFFICE
CERTIFICATE OF CORRECTION

PATENT NO. : 6,489,619 B2
APPLICATION NO. : 09/844382
DATED : December 3, 2002
INVENTOR(S) : Robert A. Street It is certified that error appears in the above-identified patent and that said Letters Patent is hereby corrected as shown below:

<u>Column 1,</u>
Line 4, insert as a new paragraph:
-- This invention was made with United States Government support under Agreement No. 70NANB7H3007 awarded by NIST. The United States Government has certain rights in this invention. --.

Signed and Sealed this

Twentieth Day of June, 2006

JON W. DUDAS
*Director of the United States Patent and Trademark Office*